United States Patent
Bianchini et al.

(10) Patent No.: US 10,973,789 B2
(45) Date of Patent: *Apr. 13, 2021

(54) COMPOSITIONS AND METHODS FOR TREATING SKIN CONDITIONS USING LIGHT AND POLYCARBOXYLIC ACIDS

(71) Applicant: Johnson & Johnson Consumer Inc., Skillman, NJ (US)

(72) Inventors: Julie Marie Bianchini, Princeton, NJ (US); Kimberly A. Capone, Lambertville, NJ (US); Kelly A. Lewis, High Bridge, NJ (US); Ali Fassih, Flemington, NJ (US); Davide Miksa, Doylestown, PA (US); Barry Setiawan, Lambertville, NJ (US); Michael D. Southall, Pennington, NJ (US); Liliam A. Moreira, Lake Hiawatha, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/790,001

(22) Filed: Feb. 13, 2020

(65) Prior Publication Data
US 2020/0179318 A1   Jun. 11, 2020

Related U.S. Application Data

(62) Division of application No. 15/427,434, filed on Feb. 8, 2017, now Pat. No. 10,596,134.

(51) Int. Cl.
| | |
|---|---|
| *A61K 31/194* | (2006.01) |
| *A61K 47/10* | (2017.01) |
| *A61K 9/70* | (2006.01) |
| *A61K 9/00* | (2006.01) |
| *A61N 5/06* | (2006.01) |
| *A61N 7/00* | (2006.01) |
| *A61P 17/10* | (2006.01) |

(52) U.S. Cl.
CPC .............. *A61K 31/194* (2013.01); *A61K 9/00* (2013.01); *A61K 9/0014* (2013.01); *A61K 9/7007* (2013.01); *A61K 47/10* (2013.01); *A61N 5/0616* (2013.01); *A61N 7/00* (2013.01); *A61P 17/10* (2018.01); *A61N 2005/0663* (2013.01); *A61N 2007/0034* (2013.01)

(58) Field of Classification Search
CPC .................................................... A61K 31/194
See application file for complete search history.

(56) References Cited

U.S. PATENT DOCUMENTS

| | | | |
|---|---|---|---|
| 7,066,941 | B2 | 6/2006 | Perricone |
| 8,758,418 | B2 | 6/2014 | Lundahl et al. |
| 8,771,328 | B2 | 7/2014 | Tapper et al. |
| 9,408,790 | B2 | 8/2016 | Bickford |
| 9,474,699 | B2 * | 10/2016 | Sun .......................... A61P 27/06 |
| 9,533,171 | B2 | 1/2017 | Greaves |
| 10,596,134 | B2 * | 3/2020 | Bianchini ............... A61P 17/10 |
| 2008/0206169 | A1 | 8/2008 | Millikin et al. |
| 2015/0182990 | A1 | 7/2015 | Binner et al. |
| 2015/0182991 | A1 | 7/2015 | Binner et al. |
| 2015/0182992 | A1 | 7/2015 | Binner et al. |
| 2015/0182993 | A1 | 7/2015 | Binner et al. |
| 2016/0045758 | A1 | 2/2016 | Tapper et al. |
| 2016/0367490 | A1 | 12/2016 | Binner et al. |

OTHER PUBLICATIONS

Neutrogena Light Therapy Acne Mask, commercially available from Johnson & Johnson Consumer Inc., Sep. 30, 2016, http://www.teenvogue.com/story/neutrogena-light-therapy-acne-mask-review.
Wheeland et al., "Evaluation of self-treatment of mild-to-moderate facial acne with a blue light treatment system", Journal of Drugs in Dermatology, Jun. 2011, 10(6):596-602, (XP002782374).
European search report dated Jul. 4, 2018, for EP application 18155767.9.

* cited by examiner

*Primary Examiner* — Rei Tsang Shiao
(74) *Attorney, Agent, or Firm* — Sharon E. Hayner

(57) ABSTRACT

The present invention provides compositions, methods and kits for treating acne and other skin conditions influenced by *P. acnes*, which combine administration of low levels of at least one C2 to C5 polycarboxylic acid and blue light to skin in need of treatment for such conditions.

9 Claims, No Drawings

COMPOSITIONS AND METHODS FOR TREATING SKIN CONDITIONS USING LIGHT AND POLYCARBOXYLIC ACIDS

CROSS-REFERENCE TO RELATED APPLICATION

This application is a divisional of U.S. application Ser. No. 15/427,434, filed Feb. 8, 2017, the disclosure of which is hereby incorporated by reference in its entirety.

FIELD OF THE INVENTION

A variety of treatments are commercially available for treating acne and other skin conditions, including compositions and devices.

Succinic acid, a polycarboxylic acid, is known to provide antimicrobial activity. It naturally occurs in plant and animal tissues. It is also produced by microbes present on human skin and is toxic to *Propionibacterium acnes*, which is implicated in the cause of acne. Succinic acid may also be made synthetically.

Light therapy is also known to be effective for treating skin conditions. In particular, it is known that blue light having a wavelength of about 400 nm to about 460 nm has an antimicrobial effect. The mechanism of antimicrobial action of blue light is thought to occur through excitation of microbial porphyrins, leading to the accumulation of intrabacterial reactive oxygen species and subsequent cell death.

U.S. Pat. No. 8,771,328 discloses improved phototherapy systems comprising a therapeutic lamp platform for radiant lamps such as LED's disposed in a convenient device that may be in the form of a facial mask. The system emits different wavelengths of radiant energy, for example at least two of blue, red, or infrared.

The NEUTROGENA Light Therapy Acne Mask, commercially available from Johnson & Johnson Consumer Inc., emits blue light to penetrate just beneath the skin's surface to kill acne-causing bacteria, and red light that penetrates deeper into the skin to reduce inflammation.

US 2008/0206169 discloses personal care compositions comprising at least one skin care active selected from a large group of compounds including succinic acid to address a large number of skin benefits. Succinic acid is said to be useful for increasing the intracellular content of glutathione, activating glutathione reductase, as an anti-oxidant, an inhibitor of tyrosinase, and a nitric oxide scavenger. The composition may be delivered in conjunction with energy via a delivery enhancement device, and the energy may be from light.

U.S. Pat. No. 7,066,941 relates to the treatment of aging or damaged skin by irradiating it with an effective amount of visible light having a wavelength of about 400 nm to about 500 nm. The light source may be sunlight or artificial light for example, and in one embodiment, light-emitting diodes are applied to discrete skin areas. Compositions containing compounds that enhance light penetration of the stratum corneum such as alpha-hydroxy acids and/or filter light may be applied to the skin prior to or during phototreatment.

However, improved skin treatments, for example acne treatments, are still needed. In particular, it would be desirable to enhance the antimicrobial activity of blue light via topical means, i.e., combining light treatment with topical agents that can potentiate the effect of light therapy. Applicants have now found that under certain conditions, short chain polycarboxylic acids boost the antimicrobial activity of blue light. Unexpectedly superior antimicrobial in particular anti-*P. acnes*, benefits are therefore achieved by administering a combination of one or more short chain polycarboxylic acids, for instance succinic acid, and blue light to skin in need of treatment.

SUMMARY OF THE INVENTION

The present invention provides a method of treating skin, comprising topically applying to skin having a condition influenced by *P. acnes* a topical composition comprising up to about 5 weight percent of at least one C2 to C5 polycarboxylic acid and exposing said skin to blue light having peak wavelength of 400 nm to 460 nm using a light delivery device.

The invention also provides a kit comprising: (a) a topical composition comprising up to about 5 weight percent of at least one C2 to C5 polycarboxylic acid, and (b) a light delivery device that delivers blue light having a peak wavelength of 400 nm to 460 nm.

The invention further provides a topical composition comprising less than about 5 weight percent succinic acid and at least about 4 weight percent glycerin.

The invention also provides a film comprising a topical composition comprising up to about 5 weight percent of at least one C2 to C5 polycarboxylic acid.

Finally, the invention provides a method of killing *P. acnes*, which comprises contacting *P. acnes* with a composition comprising up to about 5 weight percent of at least one C2 to C5 polycarboxylic acid and exposing said *P. acnes* to blue light having peak wavelength of 400 nm to 460 nm using a light delivery device.

DETAILED DESCRIPTION OF THE INVENTION

Unless defined otherwise, all technical and scientific terms used herein have the same meaning as commonly understood by one of ordinary skill in the art to which the invention belongs. All publications, patent applications, patents, and other references mentioned herein are incorporated by reference.

As used herein, "topically applying" means directly laying on or spreading on outer skin or the scalp, e.g., by use of the hands or an applicator such as a wipe, roller, or spray.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more conditions, but low enough to avoid serious side effects. The cosmetically effective amount of the compound or composition will vary with the particular condition being treated, the age and physical condition of the end user, the severity of the condition being treated/prevented, the duration of the treatment, the nature of other treatments, the specific compound or product/composition employed, the particular cosmetically-acceptable carrier utilized, and like factors.

As used herein, "cosmetically acceptable" means that the ingredients the term describes are suitable for use in contact with tissues (e.g., the skin) without undue toxicity, incompatibility, instability, irritation, allergic response, or the like.

As used herein, a "cosmetically acceptable active agent" is a compound (synthetic or natural) that has a cosmetic or therapeutic effect on the skin.

As used herein, "treatment or treating" refers to mitigating, reducing, preventing, improving, or eliminating the presence or signs of a condition or disorder.

The invention is suitable for treating skin conditions influenced by *P. acnes*. As used herein, skin conditions influenced by *P. acnes* means skin conditions to which *P. acnes* directly or indirectly contributes.

For example, the invention is suitable for treating acne. As used herein, "acne" refers to disorders resulting from the actions of hormones and other substances on the sebaceous glands and hair follicles, typically leading to clogged pores and the formation of inflammatory or non-inflammatory lesions on the skin. Specifically, it relates to blemishes, lesions, or pimples, pre-emergent pimples, blackheads, and/or whiteheads. As used herein, a "pre-emergent pimple" is an inflamed follicle that are not visually apparent on the surface of the skin with the naked eye (e.g., as a lesion).

The invention is also suitable for treating rosacea. As used herein, "rosacea" means skin with persistent erythema with or without papules, pustules, or nodules.

The invention is also suitable for treating seborrhoeic dermatitis. As used herein, seborrhoeic dermatitis means scaly, flaky, itchy, or red skin affecting the scalp, face, and torso, for instance dandruff on the scalp.

The invention is suitable for treating red patches, spots, papules, pustules, nodules, microcysts and cysts influenced by *P. acnes*.

Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

Topical Composition Comprising C2 to C5 Polycarboxylic Acid

The invention utilizes a topical composition comprising at least one C2 to C5 polycarboxylic acid. The composition may comprise one or more than one C2 to C5 polycarboxylic acid.

The topical composition may contain up to about 5 weight percent C2 to C5 polycarboxylic acid, preferably up to about 1 weight percent, or more preferably up to about 0.5 weight percent. These low levels of polycarboxylic acid typically provide only limited antimicrobial activity when used alone. However, according to the present invention, topical administration of polycarboxylic acids at these reduced levels in conjunction with exposure to blue light provides excellent antimicrobial activity.

In one embodiment, the polycarboxylic acid has an oil/water partition coefficient of −1.52 to 0.33.

In a further embodiment, the C2 to C5 polycarboxylic acid is free of major absorptions in the visible light range as measured by standard analytical methods (D. A. Skoog, D. M. West, F. J. Holler; *Fundementals of Analytical Chemistry* $7^{th}$ Ed., Saunders College Publishing, Fort Worth (1196) p. 557).

Examples of C2 to C5 polycarboxylic acids useful in the invention include acconitic acid, malonic acid, succinic acid, itaconic acid, maleic acid, and mesaconic acid.

In a preferred embodiment the C2 to C5 polycarboxylic acid is succinic acid. Succinic acid (butanedioic acid) has the chemical formula $(CH_2)_2(CO_2H)_2$. Naturally produced or synthetically produced succinic acid may be used. In one embodiment, the succinic acid is naturally produced. In another embodiment, the succinic acid is synthetically produced. For example, synthetically produced succinic acid is commercially available from EMD Performance Materials Corp.

The composition may optionally comprise a wide variety of additional oil-soluble materials and/or water-soluble materials conventionally used in compositions for use on skin, at their art-established levels. For example surfactants, pearlescent or opacifying agents, thickeners, emollients, conditioners, humectants, chelating agents, exfoliants, and additives that enhance the appearance, feel, or fragrance of the cleansing composition, such as colorants, fragrances, preservatives, pH adjusting agents, and the like, can be included.

The composition may comprise one or more other cosmetically acceptable active agents include for example anti-acne agents, shine control agents, anti-microbial agents, anti-inflammatory agents, anti-mycotic agents, anti-parasite agents, external analgesics, sunscreens, photoprotectors, antioxidants, keratolytic agents, surfactants, moisturizers, nutrients, vitamins, energy enhancers, anti-perspiration agents, astringents, deodorants, firming agents, anti-callous agents, and agents for skin conditioning.

The amount of other cosmetically active agent in may range from about 0.001% to about 20% by weight of the composition, e.g., about 0.005% to about 10% by weight of the composition, such as about 0.01% to about 5% by weight of the composition.

The cosmetically acceptable active agent may be selected for instance from, benzoyl peroxide, D-panthenol carotenoids, ceramides, polyunsaturated fatty acids, essential fatty acids, enzymes such as laccase, enzyme inhibitors, minerals, hormones such as estrogens, steroids such as hydrocortisone, 2-dimethylaminoethanol, copper salts such as copper chloride, peptides like argireline, syn-ake and those containing copper, coenzyme Q10, amino acids such as proline, vitamins, lactobionic acid, acetyl-coenzyme A, niacin, riboflavin, thiamin, ribose, electron transporters such as NADH and FADH2, natural extracts such as from aloe vera, feverfew, oatmeal, dill, blackberry, princess tree, *Picia anomala*, and chicory, resorcinols such as 4-hexyl resorcinol, curcuminoids, sugar amines such as N-acetyl glucosamines, and derivatives and mixtures thereof.

Examples of vitamins include, but are not limited to, vitamin A, vitamin B's such as vitamin B3, vitamin B5, and vitamin B12, vitamin C, vitamin K, and different forms of vitamin E like alpha, beta, gamma or delta tocopherols or their mixtures, and derivatives thereof.

Examples of antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

In one embodiment, the composition contains less than 1% by weight or less than 0.5% by weight of alpha-hydroxy acid, such as glycolic acid, lactic acid, malic acid, tartaric acid, or citric acid. In another embodiment, the composition is free of alpha-hydroxy acids.

In one embodiment, the topical composition comprises about at least about 4, or about 4 to about 20 weight percent glycerin, for example about 6 to about 10 weight percent glycerin.

In another embodiment, the topical composition comprises up to about 5 weight percent succinic acid and at least about 4 weight percent glycerin.

In another embodiment, the topical composition has a low pH of about 3.5 to about 5.5.

The composition may further include a cosmetically acceptable topical carrier. The carrier may be from about 50% to about 99.99%, by weight, of the composition (e.g., from about 80% to about 99%, by weight, of the composition). In one embodiment of the invention, the cosmetically acceptable topical carrier includes water.

The composition may be made into a wide variety of product types that include but are not limited to lotions, creams, gels, sticks, sprays, ointments, pastes, foams, powders, mousses, creams, wipes, patches, hydrogels, film-forming products, facial masks and skin masks, dissolving or non-dissolving films, and make-up such as foundations. These product types may contain a variety of cosmetically acceptable topical carriers including, but not limited to solutions, suspensions, emulsions such as microemulsions and nanoemulsions, gels, solids, films and liposomes. The following are non-limiting examples of such carriers. Other carriers can be formulated by those of ordinary skill in the art.

The composition can be formulated as a solution. Solutions typically include an aqueous or organic solvent (e.g., from about 50% to about 99.99% or from about 90% to about 99% of a cosmetically acceptable aqueous or organic solvent). Examples of suitable organic solvents include propylene glycol, polyethylene glycol, polypropylene glycol, glycerol, 1,2,4-butanetriol, sorbitol esters, 1,2,6-hexanetriol, ethanol, and mixtures thereof.

The composition may be formulated as a solution comprising an emollient. Such compositions preferably contain from about 2% to about 50% of an emollient(s). As used herein, "emollients" refer to materials used for the prevention or relief of dryness, such as by preventing the transepidermal loss of water from the skin. Examples of emollients include, but are not limited to, those set forth in the *International Cosmetic Ingredient Dictionary and Handbook*, eds. Pepe, Wenninger and McEwen, pp. 2930-36 (The Cosmetic, Toiletry, and Fragrance Assoc., Washington, D.C., 9th Edition, 2002) (hereinafter "ICI Handbook"). Examples of particularly suitable emollients include vegetable oils, mineral oils, fatty esters, and the like.

A lotion can be made from such a solution. Lotions typically contain from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically contains from about 5% to about 50% (e.g., from about 10% to about 20%) of an emollient(s) and from about 45% to about 85% (e.g., from about 50% to about 75%) of water.

The composition alternatively be anhydrous or be an ointment that includes no water but organic and/or silicone solvents, oils, lipids and waxes. An ointment may contain a simple base of animal or vegetable oils or semi-solid hydrocarbons. An ointment may contain from about 2% to about 10% of an emollient(s) plus from about 0.1% to about 2% of a thickening agent(s). Examples of thickening agents include, but are not limited to, those set forth in the ICI Handbook pp. 2979-84.

The composition may be formulated as an emulsion. If the topical carrier is an emulsion, from about 1% to about 10% (e.g., from about 2% to about 5%) of the topical carrier contains an emulsifier(s). Emulsifiers may be nonionic, anionic or cationic. Examples of emulsifiers include, but are not limited to, those set forth in the ICI Handbook, pp. 2962-71.

Lotions and creams can be formulated as emulsions. Typically such lotions contain from 0.5% to about 5% of an emulsifier(s). Such creams typically contain from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type or the oil-in-water-in-oil type, are also useful in the subject invention. In general, such single or multiphase emulsions contain water, emollients, and emulsifiers as essential ingredients.

The composition can also be formulated as a gel (e.g., an aqueous, alcohol, alcohol/water, or oil gel using a suitable gelling agent(s)). Suitable gelling agents for aqueous and/or alcoholic gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically contains between about 0.1% and 5%, by weight, of such gelling agents.

The composition can also be formulated into a solid (e.g., wax-based stick, bar, or powder).

The composition may be contained in a substrate, such as a film, woven or non-woven material, wipe, patch, mask, article of clothing and the like.

In one embodiment, the composition is contained in a film. As used herein, the term "film" means a composition that forms a thin layer or membrane on mammalian, and more particularly human skin. Such film may comprise a single layer or multiple layers.

In one embodiment the film is a dissolvable film. A variety of dissolvable films are known in the art, and any one of these may be used according to the invention.

In one particular embodiment, the film may comprise an integral film product as described in US 2015/0182991, the disclosure of which is incorporated herein by reference. The integral film product is arranged and configured to be removable from the manufacturing substrate it is made on, for use independent of the manufacturing substrate. In particular, the product may be made by placing a mask over a manufacturing substrate having a releasable surface, delivering a film-forming composition through the mask to form a raw shape on the manufacturing substrate; removing the mask; and solidifying the raw shape into the integral film product disposed on the manufacturing substrate. The mask has at least one aperture having a shape corresponding to the desired integral film product. The integral film product is arranged and configured to be removable from the releasable surface of the manufacturing substrate for use independent thereof.

In another embodiment, the film is a multilayered shaped film product as described in US 2015/0182990, the disclosure of which is incorporated herein by reference. For example, a two layer shaped film product comprising a first surface comprising the topical composition to be delivered to skin, and a second surface exposed to the exterior, may be used. Such an article of manufacture may be made using a process that comprises delivering liquid film-forming compositions through a mask; removing the mask to leave a multilayered raw shape; and curing the multilayered raw shape to form the multilayered shaped film product. The mask has a delivery surface, an opposite surface and at least one aperture having a design corresponding to the desired shaped film product. The film-forming compositions are delivered through a multistream nozzle. The movement of the mask and the delivery of the first and second liquid film-forming compositions to the mask aperture are controlled to provide a volumetric flow rate of the first and second liquid film-forming compositions to the mask aperture corresponding to the volume of a void. The nozzle is in contact with the delivery surface of the mask.

In another particular embodiment, the film may be multilayered film product as described in US 2015/0182992, the disclosure of which is incorporated herein by reference. For example, a two layer shaped film product in which a first layer has a larger surface area than a second layer disposed on the first layer may be used. This forms an "island" of the second layer on top of the first layer. One of the two layers is for contacting the skin and comprises the composition of the invention. The other layer is exposed to the exterior. Such an article of manufacture may be made by a process that comprises delivering a first film-forming composition through a first mask to form a first raw shape; removing the first mask; placing a second mask over the first raw shape; delivering a second film-forming composition through the second mask to form a second raw shape on the first raw shape; removing the second mask; and solidifying the first and second raw shapes to provide a shaped film product.

In a further embodiment, a shaped film product as described in US 2015/0182993, the disclosure of which is incorporated herein by reference, may contain the composition. Such shaped film product may be made by placing a mask over a manufacturing substrate; delivering a film-forming composition through a nozzle to form a raw shape on the manufacturing substrate; removing the mask; and solidifying the film-forming composition to provide the shaped film product disposed on the manufacturing substrate. The mask has a delivery surface and an opposite manufacturing substrate-facing surface and at least one aperture having a design corresponding to the desired shaped film product. The nozzle is disposed in sealing engagement with the delivery surface of the mask to the at least one aperture of the mask during delivery of the film-forming composition.

In yet another embodiment, a multilayer topically applied film as described in US 2016/0367490, the disclosure of which is incorporated herein by reference, may be used. This film is readily removable upon application of water thereto. As used herein, "readily removable" means the film may dissolve or disintegrate upon application of water to the film, such that it may be removed from the skin without scrubbing or the like.

Such a film comprises a first top layer having a first top surface for facing outwardly from the skin and a first bottom surface opposite the first top surface for facing towards the skin. The article also comprises a bottom skin-contacting layer comprising a second top surface facing and adhered to the first bottom surface of the first top layer and a second bottom surface that is outwardly-facing for contacting and adherence of the article to the skin when the article is applied thereto. The bottom skin-contacting layer comprises the topical composition. In addition, each of the first top layer and second bottom layer comprises a water-soluble film former and the article is readily removable from the skin upon application of water thereto. This film containing the topical composition may be formed by one of the above-described processes of forming multilayer shaped film products. It may also be made by casting and drying an adhesive layer, and then casting the top layer on top of the bottom layer. The two layers may adhere to one another by any of the known methods of adhesion (mechanical, chemical, dispersive, electrostatic, diffusive, etc.). In one embodiment, the two layers preferably are both water soluble, so that the water in the non-adhesive outwardly-facing layer will slightly dissolve the already dried adhesive skin-contacting layer, thereby creating a certain amount of diffusive adhesion at the interface of the two layers. In a second embodiment, both layers are cast wet on wet, and intermixing of the materials occurs at their interface, thereby creating a bond by diffusive adhesion. Preferably, the materials have a common solvent and/or are miscible with each other so that they intermix and bond together. It will be appreciated that the materials of the adhesive and non-adhesive layers (the skin-contacting and outwardly-facing layers, respectively) may have a common solvent other than water, such as alcohol, so that the materials bond to each other.

For example, the skin-contacting layer preferably comprises a hydrophilic film-forming polymer, a solubilizing agent to solubilize other ingredients in the film, a disintegration promoter, a thickening agent/structuring agent/texture modifier, a hydroscopic agent/wetting agent to retain skin moisture, a partition coefficient modifier/absorption- or permeation-promoting substances to drive the hydroscopic agent into skin, a plasticizer/primary adhesive agent for flexibility and softness, a solvent used for hydrocolloids and retain latent moisture and keep final article flexible and other auxiliaries or additives. The skin-contacting layer is applied preferably directly to the skin surface and possesses properties suitable for use as the skin-contacting surface of the article. Such properties include rapid dissolution, sustained adhesion strength, semi-occlusiveness, and flexibility. The skin-contacting layer comprises the polycarboxylic acid and other ingredients of the topical composition.

The outwardly-facing layer possesses proprieties suitable for use as a physical barrier, allowing it to remain clean of dust and dirt and debris while the article remains in place on the application site. Such proprieties include rapid dissolution, semi-occlusiveness, flexibility, and non-stickiness. The outwardly-facing layer comprises a hydrophilic film forming polymer, a disintegration promoter, an oil-in-water emulsifier, a wax to limit water migration from the skin-contacting layer to the topical layer, a plasticizer for flexibility and softness, a primary adhesive agent, a solvent used for hydrocolloids and to retain latent moisture and to keep the final article flexible, and other auxiliaries or additives.

In a particular embodiment of the invention, the topical composition is contained in such a multilayer, water-removable film. The film may have a thickness, for example, of up to about 2 mm. The film is placed on the skin by adhering the second bottom surface to the skin. The film is then exposed to blue light having peak wavelength of 400 nm to 460 nm using a light delivery device according to the invention. The film is maintained in place for a period of time, for example, at least 15 minutes, or at least 30 minutes, or at least 3 hours, or at least 6 hours, whereby the polycarboxylic acid is capable of transferring to the skin application site. The film is then removed from the application site by application of water, whereupon the film dissolves.

In a further embodiment of the above, the bottom skin-contacting layer further comprises an effective amount of an emulsifier to enhance transport of the polycarboxylic acid to the skin. In one embodiment, the emulsifier is a glycerine derivative. For instance, the emulsifier may be selected from the group consisting of glycerides and glycerol fatty acid esters.

Light Delivery Device

The light delivery device may comprise any source of blue light having a peak wavelength of 400 nm to 460 nm, preferably 430 nm to 450 nm. It may take any form or configuration, provided it emits blue light having a peak wavelength between 400 nm to 460 nm. The blue light may be delivered continuously, pulsed, focused, diffuse, multi-wavelength, coherent, or non-coherent within the desired range, or single wavelength.

The blue light is preferably delivered at low intensity. In one embodiment, the power delivery of blue light is less than about 20 $mW/cm^2$. For example, the blue light may be delivered at an intensity of about 1 $mW/cm^2$ to about 20 $mW/cm^2$. In another embodiment, the intensity of blue light is below about 1 $mW/cm^2$.

The light source may be for example one or more LEDs. The LEDs may be for example individual LED bulbs or multi-LED strips.

The device may be in the form of a shaped mask, shroud, or hood for use on the face. Alternatively, the device may be shaped for use on the body, in particular the torso, such as a shirt, vest, or the like. The device may be in the form or a patch having a circular, oval, rectangular, or other shape. Such a patch may also have an irregular shape, or a shape designed to fit a particular part of the face or body.

In one embodiment, the device comprises a lamp platform and remote battery pack as described in U.S. Pat. No. 8,771,328, the disclosure of which is incorporated by reference herein. The lamp platform for radiant lamps such as LEDs are disposed in an assembly comprising a first wall to which the lamps are affixed thereto and a second wall, closer to the skin, spaced from the first wall wherein the lamps are recessed relative thereto. The second wall comprises a reflective surface facing towards the skin and a plurality of light apertures substantially aligned with the LEDs on the first wall for communicating lamp radiation from the lamps to a user. The lamps and associated circuitry are disposed between the first and second wall so that the reflective surface is relatively smooth and seamless towards the skin. The number of lamps are minimized, as is the circuitry therefor, and other assembly materials are purposefully selected for a relatively light weight assembly resulting in enhanced user comfort during therapy sessions. The walls have a malleable rigidity for flexible adjustability relative to the user. More particularly, the walls have a concave configuration relative to the face of the user which is adjustable relative to a rest position to be expandable relative to a size of the head of the user for a close fitting and secure engagement to the user during use. The device is mounted to the user with a frame comprising an eyeglass frame or goggles including lenses for shielding the user's eyes from lamp radiation. The adjustability of the embodiments is further enhanced by the walls being pivotable relative to the support frame and where the frames may include telescopic temple arms for selective adjustability relative to the head size of the user. The device is thus supported on the patient as a wearable hands-free mask or the like. A power source communicates energy to the lamps and comprises a remote battery pack and may also include a control processor for counting the number of uses by the device for the user and for indicating a need for device replacement after a predetermined number of uses.

The platform can be secured to the head by multiple means: eyeglass frames, straps, drawstring, harness, VELCRO, turn dial or snap and buttons. As the mask is secured it can be adjusted upward, for chin to forehead coverage. It can also be adjusted outward, for side-to-side coverage. In addition, once the platform has been bent/slid to cover the face area, the distance of the platform from the skin can be adjusted for achieving a desired light intensity relative to a user's skin surface. Thus, the light therapy can be maximized in up to three physical dimensions.

The subject adjustability may be implemented through "smart" processing and sensor systems for enhanced flexibility/adjustability in the form of adjustable energy output, adjustable wavelengths, priority zones, timers, and the like. The sensors of the sensor systems will enable the subject embodiments to have the ability to evaluate the skin of the face and body of a patient with sensors for color, acne, lesion density, and the like, and plan a smart treatment, utilizing more or less energy on the priority zones. The subject embodiments can be smart from the standpoint of skin type, age, overall severity of problems and have the ability to customize the treatment accordingly.

In another embodiment, the device comprises a therapeutic lamp platform for radiant lamps such as LED's disposed in a holdable spot applicator assembly, as described in US 2016/0045758, the disclosure of which is incorporated by reference herein. The holdable spot applicator assembly includes a reflective surface facing towards a patient and a plurality of LED's for communicating lamp radiation from the lamps to a user. The lamps and the associated circuitry are housed within a holdable elongated structure.

In one embodiment, ultrasonic energy is also delivered to the skin, concurrently or in series with the blue light. The ultrasonic energy may be delivered by the light device or by a separate device.

In one embodiment, the light delivery device delivers both light and ultrasonic energy.

Anti-Microbial Activity

According to the invention, administration of a combination of C2 to C5 polycarboxylic acid and blue light provides increased antimicrobial, in particular increased anti-*P. acnes* activity. It has been found that such combinations provide synergistic anti-*P. acnes* activity relative to the anti-*P. acnes* activity shown by either topical administration of succinic acid alone or exposure to blue light alone.

In one embodiment, the combination provides at least a 2 Log reduction of *P. acnes* over the activity of either treatment alone.

Reduction of *P. acnes* is measured by the following in vitro method.

*Propionibacterium acnes* ATCC 6919 is grown in reinforced clostridial medium (RCM) with 100 ppm of 6-aminolevulinic acid (ALA) added. The culture is incubated in anaerobic chamber (<10 ppm $O^2$, 2.5-5% $H^2$, balance $N^2$ at 35±2° C.), in the dark, on an orbital shaker at 80 RPM to a concentration of approximately $10^8$ colony forming units/ml (cfu/ml). For test treatments including light, the prepared *P. acnes* culture is exposed for two, 60-minute light cycles with a 60-minute hold time between. Each light cycle is with blue light at wavelength 440 nm and 22±2 $mW/cm^2$ intensity. After treatments, the sample is incubated overnight (16±2 hours) in an anaerobic chamber. The sample is then recovered onto agar and incubated 5-7 days until clear colonies are visible. After growth, the remaining viable P. acnes colonies are counted; converted to cfu/ml and the log 10 reduction in number of cells is calculated (log 10 reduction=no light control sample−test sample).

The C2 to C5 polycarboxylic acid-containing composition and the blue light may be administered to the skin simultaneously or sequentially. When administered sequentially, the composition and blue light may be administered in either order. When administered with ultrasonic energy as well, the composition, blue light, and ultrasonic energy may be administered simultaneously or in any order.

In one embodiment of the invention, skin in need of treatment for acne is treated by topically applying to the skin a composition comprising up to about 5 weight percent of succinic acid and exposing the skin to blue light having a wavelength of about 440 nm using a light delivery device.

In another embodiment of the invention, skin in need of treatment for rosacea is treated by topically applying to the skin a composition comprising up to about 5 weight percent of succinic acid and exposing the skin to blue light having a wavelength of about 440 nm using a light delivery device.

In another embodiment of the invention, skin in need of treatment for eczema is treated by topically applying to the skin a composition comprising up to about 5 weight percent of succinic acid and exposing the skin to blue light having a wavelength of about 440 nm using a light delivery device.

In a further embodiment of the invention, skin in need of treatment for psoriasis is treated by topically applying to the skin a composition comprising up to about 5 weight percent of succinic acid and exposing the skin to blue light having a wavelength of about 440 nm using a light delivery device.

The following non-limiting examples further illustrate the invention.

Example 1

The anti-P. acnes activity of various test treatments were compared. Anti-P. acnes activity was measured using the in vitro method described above. The test treatments comprised either 0.1 or 0.25 weight percent of succinic acid in reinforced clostridial media with and without the administration of 440 nm blue light. Anti-P. acnes activity was also studied on an untreated reinforced clostridial broth culture control. Non-control test samples were adjusted to a pH of 4.5.

The results are shown in Table 1.

TABLE 1

| Test Treatment | Log 10 reduction vs Control Solution |
|---|---|
| Control solution - no light | 0 |
| 0.1% Succinic Acid - no light | 2.0 |
| 0.25% Succinic Acid - no light | 5.6 |
| Control solution + light | 0.6 |
| 0.1% Succinic Acid + light | >6.7 |
| 0.25% Succinic Acid + light | >6.7 |

These results show that succinic acid anti-P. acnes efficacy is synergistically enhanced when combined with blue light. For example, compared to untreated control solution, 0.1% succinic acid reduced P. acnes bacterial count by 2 logs, and light alone reduced P. acnes bacterial count by 0.6 logs. If the effects of these individual treatments were additive, one would expect a 2.6 log reduction in bacterial count. However when light was combined with succinic acid, the P. acnes bacterial count was reduced by 6.7 logs, indicating synergistic antimicrobial activity of light and succinic acid. A 6.7 log reduction represents about 12,000 times greater antimicrobial activity than a 2.6 log reduction. Additionally, for example, compared to untreated control solution, 0.25% succinic acid reduced P. acnes bacterial count by 5.6 logs, and light alone reduced P. acnes bacterial count by 0.6 logs. If these individual treatments were additive, one would expect a 6.2 log reduction in P. acnes bacterial count. However, when light was combined with 0.25% succinic acid, the P. acnes bacterial count was reduced by 6.7 logs, indicating synergistic anti-P. acnes activity of light and succinic acid. A 6.7 log reduction represents about 3 times more antimicrobial activity than a 6.2 log reduction Example 2

The following topical compositions according to the invention containing succinic acid and glycerin were prepared using the ingredients shown in Tables 2 and 3.

TABLE 2

| Ingredient Name | % w/w |
|---|---|
| Cetearyl Olivate | 0.30 |
| Chlorphenesin | 0.20 |
| Dimethicone | 5.62 |
| Dimethicone Crosspolymer | 0.20 |
| Dimethiconol | 0.18 |
| Ethylhexylglycerin | 0.08 |
| Fragrance | 0.10 |
| Glycerin | 8.00 |
| Phenoxyethanol | 0.72 |
| Polyacrylate 13 | 0.90 |
| Polyacrylate Crosspolymer 6 | 0.80 |
| Polyisobutene | 0.42 |
| Polysorbate 20 | 0.08 |
| Purified Water | q.s. |
| Sodium Hydroxide | pH adjuster |
| Sorbitan Olivate | 0.20 |
| Sorbitan Stearate | 0.06 |
| Succinic Acid | 0.50 |

TABLE 3

| Ingredient Name | % w/w |
|---|---|
| Cetearyl Olivate | 0.30 |
| Chlorphenesin | 0.20 |
| Dimethicone | 5.65 |
| Dimethicone Crosspolymer | 0.20 |
| Dimethiconol | 0.15 |
| Ethylhexylglycerin | 0.08 |
| Glycerin | 12.00 |
| Phenoxyethanol | 0.72 |
| Polyacrylate 13 | 0.90 |
| Polyacrylate Crosspolymer 6 | 0.80 |
| Polyisobutene | 0.42 |
| Polysorbate 20 | 0.08 |
| Purified Water | q.s. |
| Sodium Hydroxide | pH adjuster |
| Sorbitan Olivate | 0.2 |
| Sorbitan Stearate | 0.06 |
| Succinic Acid | 1.00 |

Example 3

Blue light having a wavelength of 440 nm and an intensity of 0.8 mW/cm$^2$ was directed through a polymethylmethacrylate (PMMA) plate (HELIOPLATE HD6 from Helio-Screen Labs), which mimics the human skin surface. The intensity of the light that penetrated through the plate was measured using a Newport Power Meter (Model 1936-R) and compared before and after coating the plate with the topical composition described in Table 2 at a thickness of 1 µL/cm$^2$. The results are shown in Table 4.

TABLE 4

| Experimental Condition | Intensity of Blue Light (440 nm) Measured |
|---|---|
| Without topical composition | 0.7500 mW ± 0.01421 |
| With topical composition | 0.79075 mW ± 0.00171 |

The results show the light penetration through the PMMA plate was enhanced by an average 5.46% from four experiments with application of the topical composition. In addition, such a composition administered with blue light having a peak wavelength of 400 nm to 460 nm will provide enhanced antimicrobial activity and enhanced anti-acne activity.

The invention claimed is:

1. A kit comprising: (a) a topical composition comprising up to about 5 weight percent of at least one C2 to C5 polycarboxylic acid selected from the group consisting of acconitic acid, malonic acid, succinic acid, itaconic acid, maleic acid, and mesaconic acid, and (b) a light delivery device that delivers blue light having a peak wavelength of 400 nm to 460 nm.

2. The kit of claim 1, wherein the topical composition comprises up to about 1 weight percent of the polycarboxylic acid.

3. The kit of claim 1, wherein the polycarboxylic acid is succinic acid.

4. The kit of claim 1, wherein the topical composition comprises about 4 to about 20 weight percent glycerin.

5. The kit of claim 1, wherein the topical composition has a pH of 3.5-5.5.

6. The kit of claim 1, wherein the intensity of the light delivered is below about 20 mW/cm$^2$.

7. The kit of claim 1, wherein the intensity of the light delivered is below about 2 mW/cm$^2$.

8. The kit of claim 1, wherein the light delivery device also delivers ultrasonic energy.

9. The kit of claim 1, wherein the topical composition is contained in a film.

* * * * *